United States Patent [19]

Mori et al.

[11] Patent Number: 5,053,228

[45] Date of Patent: Oct. 1, 1991

[54] POLYMERIC TEMPERATURE SENSITIVE DRUG CARRIER

[75] Inventors: Yuichi Mori; Toshiya Sakai, both of Kanagawa, Japan

[73] Assignee: W. R. Grace & Co.-Conn., New York, N.Y.

[21] Appl. No.: 552,042

[22] Filed: Jul. 13, 1990

[30] Foreign Application Priority Data

Aug. 18, 1989 [JP] Japan .................................. 1-212855

[51] Int. Cl.$^5$ ....................... A61K 9/08; A61K 31/78; A61K 31/765
[52] U.S. Cl. ...................................... 424/486; 424/78; 424/81; 424/487; 523/122
[58] Field of Search ...................... 424/78, 81, 486, 87; 523/122

[56] References Cited

U.S. PATENT DOCUMENTS

| | | | |
|---|---|---|---|
| 4,182,695 | 1/1980 | Horn et al. | 424/78 |
| 4,609,707 | 9/1986 | Nowinski et al. | 525/54.1 |
| 4,780,409 | 10/1988 | Monji et al. | 435/7 |
| 4,829,098 | 5/1989 | Hoffman et al. | 435/179 |
| 4,912,032 | 3/1990 | Hoffman et al. | 435/7 |

OTHER PUBLICATIONS

Hoffman et al., "Thermally Reversible Hydrogels: Delivery and Selective Removal of Substances from Aqueous Solutions," Journ. of Controlled Release, 4:213–222, 1986.
Bae et al., "Thermo-Sensitive Polymers as On–Off Switches for Drug Release," Makromol. Chem., Rapid Commun., 8:481–485, 1987.

Primary Examiner—Thurman K. Page
Assistant Examiner—Edward J. Webman
Attorney, Agent, or Firm—Vanessa L. Appleby; Jill H. Krafte; Steven T. Trinker

[57] ABSTRACT

The drug carrier of this invention provides a temperature-sensitive polymer chemically bonded to a drug. The drug carrier is capable of releasing a drug continuously in the body. The drug carrier is a liquid when administered and becomes solid in the body, in which state it is capable of releasing a drug continuously. The drug carrier has a lower LCST than human body temperature.

4 Claims, No Drawings

POLYMERIC TEMPERATURE SENSITIVE DRUG CARRIER

TECHNICAL FIELD

This invention relates to a drug carrier capable of releasing a drug continuously in the body. More particularly, it relates to a drug carrier which is easily administered by virtue of being a liquid at the administered temperature, and capable of releasing a drug continuously by virtue of being a solid in the body.

BACKGROUND ART

In recent years, the development of a drug delivery system (DDS) which maximizes the drug effect and minimizes the side effects has been sought. DDS can be classified according to morphology and methods of administration as follows.

1) A system in which a drug is complexed to a polymeric membrane or formed as a molded product and is adhered on skin or a mucous membrane for slow release or absorption of the drug through the skin or the mucous membrane, respectively.
2) A body implant system in which a drug complexed to various forms of matrix is left in an organ or subcutaneous tissues for slow release.
3) A system in which a drug microencapsulated by means of liposome or lipid microspheres or a prodrug formed by covalently bonding a drug to a polymeric compound is administered directly in blood or tissues.

As an example the body implant system described in #2 above, an anti-cancer agent is complexed to a polymeric carrier. The implant is applied to the cancerous host and the anti-cancer agent is released continuously. The implant has been developed to reduce the size of tumor, extend the life and relieve pain caused by the cancer. This system has been applied to drugs other than anti-cancer agents, for example anesthetics, narcotic antagonists, immunoactivators such as interleukin, and interferons, and various hormones. In body implants, a drug is dispersed in polymeric matrix mainly by physical means, and allowed to diffuse from the interior of the matrix to carry out a slow release. Because certain drugs can be readily complexed to the matrix, the technology is applicable to a broad range of drugs. Another advantage of the system is that there is very little loss of activity of the drug during the manufacturing process.

The clinical application of these body implants requires implantation by a surgical means in a form suitable for its application, such as needles, rods, films or pellets. The polymeric matrix can include polymers which do or do not degrade in the body. In the case of a matrix which does not decompose in the body, the implant has to be extracted by surgical method after releasing the drug contained therein. Thus, the implants that must be removed surgically are not desirable for clinical application because of pain, infection, and scar formation that might be imposed on the patient.

Additionally, the action of the drug being released from an implant left in the body tends to be limited to the region in contact with the implant. Therefore, distribution of the drug in the focus region tends to be nonuniform.

Further, an implant embedded in the body may act as an antigen. The implant may be recognized by the body as a foreign substance, and a capsulation consisting of the tissue components is formed around the implant as a defense mechanism. As a result, the efficiency of delivery of the drug to the focus is reduced further. Thus, the body implant system has numerous problems.

Drugs microencapsulated in liposome or lipid microspheres as described in #3 above are being developed in an effort to overcome the problems associated with body implants. Microencapsulated drugs can be administered directly into blood or tissues without requiring surgical treatment. Certain products of this type are being developed and used clinically. Examples are oil-soluble drugs such as steroids, indomethacin, prostaglandin and so on, mixed into lipid microspheres, and water-soluble anti-cancer drugs such as adriamycin or mitomycin or water-soluble hormones such as insulin, microencapsulated in a liposome.

The lipid microsphere is a droplet of soybean oil, coated with a monolayer film of lecithin. Therefore, this application is only useful for drugs which are soluble in soybean oil, and not useful for water-soluble drugs. Also, because lipid microspheres are prepared by suspending soybean oil and lecithin in water, particle size is large and uneven, and thus it is difficult for the product to be distributed uniformly and broadly when it is injected into tissue. Further, the drug being incorporated in lipid microspheres is released by a diffusion process through the oil droplet. Thus, the rate of release decreases in exponential manner, and continuous release at a constant rate is difficult.

Similar to the situation with lipid microspheres, it is difficult to manufacture liposome products with a uniform particle size and to achieve a uniform or broad distribution of the drug when injected in the tissues. Also, there are problems with stability during storage and mechanical strength of the product, making it difficult to maintain the slow-releasing property of the drug for a lengthy period of time.

Accordingly, prodrugs, i.e., drugs that are chemically linked to a polymer, via covalent bonds in particular, have been developed in recent years. This technology has attempted to achieve the following goals.

1) Enhancement of ease of use of a drug by improvement of the chemical and biological properties.
2) Increasing the stability of the products in the body, such as in blood or tissues.

Specifically, a drug with low solubility is made more soluble in water by linking to a water-soluble polymer such as dextran or poly-N-(2-hydroxy-propyl) methacrylamide and so on, to facilitate its delivery. Or, by conversion of a drug into a polymer, its excretion from liver and kidney has been suppressed and its retention time in blood or in tissue has been extended. In this case, drug effect is expressed by release of the drug from the polymer by hydrolysis and the rate of slow release is controlled by the rate of hydrolysis.

Water-soluble prodrugs, unlike body implants, can be delivered uniformly into the blood or tissues by a simple method such as injection. However, due to the water soluble nature of the prodrug, after being injected into the body, it has a significantly faster rate of disappearance from the blood or tissues than the body implant or the microencapsulated drug. It is also known that the drugs covalently bonded to water-soluble polymers have a significantly faster rate of hydrolysis than drugs bonded to water-insoluble polymers.

Although prodrugs covalently bonded to water-soluble polymers have an advantageous way of administration, it is difficult to maintain a slow-releasing property for a lengthy period of time. On the other hand, water-insoluble prodrugs are advantageous from the standpoint of slow-releasing properties, but present difficulty in delivery of the drugs.

To date, a drug carrier that is easy to administer and can fully satisfy the requirement for slow release of the drug has not been provided. The objective of this invention is to provide a drug carrier that can be administered easily and can maintain a uniform concentration for a long period of time in the tissues.

DETAILED DESCRIPTION OF THE INVENTION

The objective of this invention can be attained by means of a drug carrier comprising a drug chemically bound to a temperature-sensitive polymeric compound having a lower LCST than human body temperature. LCST (lower critical solution temperature) refers to the transition temperature of the polymeric compound between hydration and dehydration.

The temperature-sensitive polymeric compound of this invention is a polymeric compound that has a negative temperature coefficient of solubility in water and has the following additional characteristics. The hydrate (oxonium hydroxide) formed at lower temperature by hydrogen bonding between the polymeric compound and water molecules decomposes at a higher temperature; this is followed by accumulation of the polymeric compound as a result of dehydration, and finally by precipitation of the polymeric compound. As mentioned above, the transition temperature between hydration and dehydration is referred to as LCST. The polymeric compound undergoes accumulation at a temperature higher than the LCST, solidifies and again dissolves in water at a temperature lower than LCST.

The present invention focuses on such a property of the temperature-sensitive polymeric compounds and perfects the drug carrier wherein a drug is chemically bonded to the temperature-sensitive polymeric compound.

A characteristic of the drug carrier of this invention is that LCST of the temperature-sensitive polymer chemically bonded to the drug is lower than the human body temperature (about 37° C.). That is, the drug carrier is in an uniform state of solution at the time of administration, but precipitates when delivered into the body.

Additionally, because the drug carrier of this invention is uniformly liquid at the time of administration, it is possible to administer it conveniently by a procedure such as injection. Furthermore, it is possible to distribute the drug uniformly throughout the tissues if it is administered topically to the target organ.

The drug carrier of this invention will remain in the body longer when administered and subjected to a temperature higher than the LCST of the drug carrier, i.e., body temperature, and becomes insoluble and precipitates. Therefore, it can achieve slow release and a better targeting of the drug when administered in a target organ, and so on.

Because the temperature-sensitive polymeric compound in the drug carrier of this invention becomes insoluble, i.e., hydrophobic, in the body, the rate of hydrolysis of the covalent bond between said polymer and the drug declines slowly and the drug is released continuously over a longer period of time, which is characteristic of this invention.

It is further possible to re-dissolve the drug-released polymeric compound in body fluid to facilitate its excretion. This is accomplished by setting the LCST of the drug carrier of this invention in such a way that it is lower than the body temperature when chemically bonded to the drug but higher than the body temperature after releasing the drug. In this case, molecular weight of the temperature-sensitive polymeric compound has to be appropriate to allow the polymer to be excreted by kidney and liver, preferably smaller than about 50,000.

Another important characteristic of the drug carrier of this invention is as follows. Because the surface of the insoluble material or precipitate from which the drug has been liberated by hydrolysis becomes soluble and dissolves in the body fluid, the drug releasing process is a surface errosion type and the rate of release remains constant. Thus, even a drug with a narrow therapeutic range can maintain an effective concentration without a side effect for a longer period of time than the conventional diffusion type system where the rate of release decreases exponentially.

Further, unlike the body implants, the drug carrier of this invention is not immunogenic and is not completely immobilized to organ or tissues where it resides. Therefore, the drug carrier of this invention can increase the biological utilizability greater than the conventional drug carriers.

Any temperature-sensitive polymeric compounds can be used widely in this invention as long as they are nontoxic and the LCST is lower than the body temperature when bonded with the drug. Examples of such temperature-sensitive polymeric compounds are poly(N-substituted acrylamide) derivatives, poly(N-substituted methacrylamide) derivatives, their copolymers, polymethylvinyl ether derivatives or partially acetylated polyvinyl alcohol derivatives and so on.

Preferred temperature-sensitive polymeric compounds have LCST higher than room temperature but lower than the body temperature when bonded with the drug. By selecting such compounds, management of temperature during administration can be easily maintained. Even more preferred are the polymeric compounds where the LCST after releasing the chemically bonded drug is higher than the human body temperature. If the drug carrier of this invention has the aforesaid property, it can be excreted easily because it can re-dissolve after releasing the drug.

Polymers suitable as the temperature-sensitive polymeric compounds of the drug carrier of this invention are illustrated below by examples, but are not limited to these examples. Incidentally, the LCST of these polymers increases in the order given blow.

Poly-N-acryloyl piperidine
Poly-N-n-propyl methacrylamide
Poly-N-isopropyl acrylamide
Poly-N,N-diethyl acrylamide
Poly-N-isopropyl methacrylamide
Poly-N-cyclopropyl acrylamide
Poly-N-acryloyl pyrrolidine
Poly-N,N-ethylmethyl acrylamide
Poly-N-cyclopropyl methacrylamide
Poly-N-ethyl acrylamide Aforesaid polymeric compounds may be homopolymers or copolymers with other monomers. Hydrophilic and hydrophobic monomers can be used as the monomers to be copolymerized. Generally speaking, copolymerization with hydrophilic monomers will raise the LCST and copolymerization with hydrophobic monomers will lower the LCST. Therefore, LCST can be controlled to any desirable level by selecting a proper monomer.

Examples of hydrophilic monomers are N-vinyl pyrrolidone, vinylpyridine, acrylamide, methacrylamide, N-acrylamide, hydroxyethyl methacrylate, hyroxyethyl acrylate, hydroxymethyl methacrylate, hydroxymethyl acrylate, acrylic acids and methacrylic acids having acidic groups and their salts, vinylsulfonic acids, styrenesulfonic acids and so on, N,N-dimethylaminoethyl methacrylate, N,N-diethylaminoethyl methacrylate, and N,N-dimethylaminopropyl acrylamide having basic groups and their salts, and so on, but not limited to these examples.

Examples of hydrophobic monomers are acrylate- and methacrylate derivatives such as ethyl acrylate, methyl methacrylate, and glycidyl methacrylate and so on, N-substituted alkyl (meth)acrylamide derivatives such as N-n-butyl (meth)acrylamide and so on, vinylchloride, acrylonitrile, styrene, and vinyl acetate and so on, but not limited to these examples.

Particularly preferred partial acetylated polyvinyl alcohol has 30–50% as its degree of acetylation.

There is no particular problem with respect to the type of bonding, as long as the temperature-sensitive polymeric compound and the drug are attached by chemical bond in this invention. However, it is desirable that the bond is a hydrolyzable covalent bond such as ester bond, amide bond, urethane bond, urea bond, carbamate bond, thiol ester bond and hydrazone bond, and so on, because with such bonds, the drug can be released slowly from the polymer carrier in the body by hydrolysis, to produce its pharmacological activity. Also, it is desirable that the type of chemical bond is selected in such a way that the chemical structure of the drug to be released after the hydrolysis is identical to the chemical structure of the drug before bonding or the structure that has pharmacological activity.

The chemical bond in this invention between the temperature-sensitive polymeric compound and the drug may be formed by chemically reacting the drug with the polymeric compound or by polymerizing the monomer that contains the drug.

Examples of the methods of preparation of polymeric compound covalently bonded to the drug are illustrated below, but are not limited to these examples. To form an ester bond, a monomer containing an ester bond in the side chain is synthesized by condensation of the hydroxyl group in the drug and acryl chloride, as described in Japanese patent SHO 39-20510 (1964), and subsequently this monomer is copolymerized with a N-substituted (meth)acrylamide derivative, to carry the drug on the polymer by means of the ester linkage. Or, as described in *Dokl. Akad. Nauk, SSSR*, Volume 141, page 1117 (1961), a drug having carboxyl group is converted into an acyl chloride and an ester bond is formed by polymer reaction with polyvinyl alcohol.

To form an amide bond, as described in *J. of Bioactive Biocompartible Polymer*, Volume 2, April issue, page 120 (1987), a monomer containing an amide bond in its side chain is synthesized by condensation reaction of the amino group in the drug and the acryl chloride, and subsequently this monomer is copolymerized with a N-substituted (meth)acrylamide derivative. Or, as described in *Farmaco. Ed. Sci.*, Volume 32, page 220 (1977), it is possible to form an amide bond by polymer reaction of the amino group-containing drug with a carboxylic acid derivative-containing polymer.

As described in *Life Science*, Volume 18, page 977 (1976), the hydrazone bond can be formed by polymer reaction of a drug having ketone group and a polymer containing hydrazine group.

For urethane bond, as described in *J. Med. Chem.*, Volume 16, No. 5, page 573 (1973), a phosgene is reacted with a hydroxyl group-containing polymer to form a corresponding chlorocarbonate compound, and subsequently the urethane bond can be formed by polymer reaction of a drug containing amino group and the chlorocarbonate compound.

This invention can be applied broadly on many drugs which need to be released slowly, and there is no limit as to which drug it can be applied. This invention is particularly useful for anti-cancer agent, hormones, antibiotics, narcotic antagonists, analgesics, anesthetics, anti-inflammatory agent, hypotensives, anti-depressants, anti-epileptic agents, anti-malarial agents, antihelmintics or immunoactivaters and so on.

Because the drug carrier of this invention is a liquid at the temperature where administration is made, it can easily be administered orally, by injection or by injection using a catheter. In addition, because the drug carrier of this invention can control the release of drug and increase the biological utilization ratio, it can maintain a continuously effective concentration of the drug, can show the maximum drug effect, and reduce its side effects.

This invention is explained further by way of examples.

EXAMPLE 1

N-Isopropyl acrylamide monomer (NIPAAm) 5 g and estrone acrylate [prepared by the method disclosed in Japanese patent SHO 39-20510 (1964)]1.6 g were dissolved in tetrahydrofuran (THF) 50 ml. 2,2'-Azobisisobutyronitrile (AIBN) 0.021 g was used as the polymerization initiator, to run the polymerization reaction at 50° C. in a stream of nitrogen gas for 12 hours, with constant agitation. The reaction mixture was re-precipitated and purified with ethyl ether. The LCST of the 1% solution of estrone-containing polymer in phosphate buffer was lower than 37° C. Estrone content of this substance was 38 weight %.

This polymer 10 mg was dissolved in pH 7.4 phosphate buffer 10 ml, and the temperature was kept at 37° C. Samples were taken from the reaction mixture at certain intervals, and the amount of estrone being released was examined by high speed liquid chromatography. Estrone was released very slowly from this polymer. Thus, about 20% of the estrone was released in 2 weeks.

EXAMPLE 2

N-Isopropyl acrylamide (NIPAAm) 5 g and 1-N-methacryloyl-5-fluorouracil (MAFU) 0.97 g were dissolved in acetonitrile 50 ml. 2,2'-Azobisisobutyronitrile (AIBN) 0.021 g was used as the polymerization initiator to run the polymerization reaction at 50° C. in a stream of nitrogen gas for 24 hours, with constant agitation. The reaction mixture was re-precipitated and purified with ethyl ether. Yield of target compound was 1.8 g. Content of 5-fluorouracil in this substance, as determined by element analysis, was 20 weight %. And, LCST of the 1% polymer solution in phosphate buffer was lower than 37° C.

This 5-fluorouracil-containing polymer 10 mg was dissolved in 10 ml pH 7.4 phosphate buffer, and the solution was kept at 37° C. Samples were taken from the reaction mixture at certain intervals, and the amount of 5-fluorouracil being released was determined by high speed liquid chromatography. 5-Fluorouracil was released very slowly, and about 20% of the 5-fluorouracil was released in 2 weeks. Release of the drug was extremely slower than the conventional polymer-supported 5-fluorouracil.

EXAMPLE 3

N-Isopropyl acrylamide (NIPAAm) 0.5 g and (1-N-methacryloyl-ε-amino-caproyl)-benzotriazole [prepared by the method disclosed by P. Ferrufi in *Farmaco., Ed. Sci.,* Volume 32, page 220 (1977)] 0.094 g were dissolved in dioxane 5 ml. 2,2'-Azobisisobutyronitrile 0.002 g was used as the polymerization initiator, to run the polymerization reaction at 50° C. in a stream of nitrogen gas for 12 hours, with constant agitation. The reaction mixture was re-precipitated and purified with ethyl ether. The acquired copolymer containing active ester group in the side chain and mitomycin C 100 mg were dissolved in dimethylformamide (DMF) 5 ml, and reaction was carried out at room temperature in a stream of nitrogen gas for 12 hours, with constant agitation. Reaction mixture was diluted with water 5 ml, and dialyzed against water, concentrated, and acetone was added to the concentrate to precipitate the desired product. Mitomycin C content in this substance was 10 weight %.

This polymer 10 mg was dissolved in 10 ml pH 7.4 phosphate buffer 10 ml, and the solution was kept at 37° C. Samples were taken from the reaction mixture at certain intervals, and the amount of mitomycin released was examined by high speed liquid chromatography.

Mitomycin C was released very slowly from this polymer. Thus, about 30% of the drug was released in one week.

EXAMPLE 4

N-Isopropyl acrylamide monomer (NIPAAm) 5 g and 1-0-(4-methacryloylaminophenyl)-β-D-glucopyranoside [prepared by the method described by Carpino, et al., in *Makromol. Chem.,* Volume 175, page 1007 (1974)] 1.55 g were dissolved in dimethylformamide 50 ml. 2,2'-Azobisisobutyronitrile (AIBN) 0.2 g was used as the polymerization initiator, to run a polymerization reaction at 50° C. in a stream of nitrogen gas for 12 hours, with constant agitation. The reaction mixture was re-precipitated and purified with ethyl ether. Subsequently, this polymer was converted into a hydrazine derivative by the method known in the prior art [Pasternak et al., *Life Science,* Volume 18, page 977 (1976)]. Thus, 1.1 ml of the aqueous sodium periodate solution (10%) was added to 5.0 g of the polymer in 50 ml of acetone, and oxidation reaction was carried out at room temperature. It was filtered and then dried, to acquire an aldehyde derivative. This aldehyde derivative was dissolved in ethanol 50 ml. Aqueous hydrazine solution (85%) 0.15 ml was added, and reaction was carried out at room temperature for 6 hours to acquire the hydrazone derivative. This compound was then reduced with 1.5 ml of aqueous sodium borohydride solution (10%) at 4° C., to acquire the hydrazine derivative. This hydrazine derivative was added with 1.5 g of naloxone in dimethyl formamide 25 ml, and reaction was carried out at room temperature in a stream of nitrogen gas for 12 hours, with constant agitation. Reaction mixture was re-precipitated and purified with ethyl ether, and the yield of the desired product was 2.5 g. naloxone content in this substance was 20 weight %.

This polymer 10 mg was dissolved in pH 7.4 phosphate buffer 10 ml, and the solution was kept at 37° C. Samples were taken from the reaction mixture at certain intervals, and the amount of naloxane (sic) released was examined by high speed liquid chromatography. Naloxone was released, from this polymer very slowly. About 20% of the naloxone was released in one week.

EXAMPLE 5

Partially acetylated polyvinyl alcohol [prepared by the method described by Sakurada et al., in *Kobunshi Kagaku,* Volume 14, No. 141, page 41 (1957), degree of acetylation=30 mol %] 5 g, 4-dimethylaminopyridine 0.24 g, and p-aminosalicyl chloride 0.19 g [prepared by the method described by S. N. Ushakov et al., in *Dokl. Akad. Nauk, SSSR,* Volume 141, page 1117 (1961)] were dissolved in dimethylformamide 100 ml, and a reaction was carried out at room temperature in a stream of nitrogen gas for 6 hours, with constant agitation. Acetone was added to the reaction mixture to precipitate the polymer. Yield of polymer was 33 g. Content of p-aminosalicylic acid (PAS) in this polymer was 22%.

This polymer 10 mg was dissolved in pH 7.4 phosphate buffer 10 ml, and the solution was kept at 37° C. Samples were taken from the reaction mixture at certain intervals, and the amount of PAS released was examined by high speed liquid chromatography. PAS was released very slowly from this polymer. Thus, about 30% of the PAS was released in 2 weeks.

EXAMPLE 6

A toluene solution (25 ml) containing 12.4% phosgene was added dropwise at 4° C. to 50 ml of pyridine solution containing partially acetylated polyvinyl alcohol 5 g [prepared by the method described by Sakurada et al., in *Kobunshi Kagaku,* Volume 14, No. 141, page 41 (1957), degree of acetylation=30 mol %], and then the mixture was agitated at room temperature for 48 hours. Excess phosgene was removed under a reduced pressure, and thus a chloroformate was obtained. A chloroform solution (10 ml) containing 0.95 g of N-(4-aminobenzenesulfonyl)-N'-butyl urea was added dropwise at 4° C. into the tetrahydrofuran solution (50 ml) containing the above compound and triethylamine 0.35 g, and a reaction was carried out at room temperature for 12 hours. Ethyl ether was added to the reaction mixture, and then it was filtered. Filtrate was concentrated, and then THF-ethyl ether was added to re-precipitate and purify the product. Thus, 2.5 g of the polymer was obtained. LCST of the polymer in 1% phosphate buffer solution was lower than 37° C.

This polymer 10 mg was dissolved in phosphate buffer 10 ml, and the mixture was kept at 37° C. Samples were withdrawn from the reaction mixture at certain intervals, and the amount of the drug released was examined by high speed liquid chromatography. The drug was released slowly from this polymer. Thus, 20% of N-(4-aminobenzenesulfonyl)-N'-butyl urea was released in one week.

What is claimed is:

1. A method for administering a slow release drug to a patient comprising:

(a) selecting a temperature-sensitive polymeric compound,
(b) selecting a drug,
(c) forming a hydrolyzable covalent bond between said polymeric compound and said drug, wherein the resulting polymer/drug compound has a lower LCST than body temperature, and
(d) administering said polymer/drug compound to a patient wherein the liquid solution of said polymer/drug compound is at a temperature lower than body temperature.

2. A method of claim 1 wherein said polymeric compound in a poly(N-substituted acrylamide), a poly(N-substituted methacrylamide), their copolymers, a polymethylvinyl ether or a partially acetylated polyvinyl alcohol.

3. The method of claim 1 wherein said covalent bond is an ester bond, amide bond, urethane bond, urea bond, carbamate bond, thiol ester bond or hydrazone bond.

4. The method of claim 1 wherein said drug is an anti-cancer agent, hormone, antibiotic, narcotic antagonist, analgesic, anti-inflammatory agent, hypotensive, anti-depressant, anti-epileptic agent, anti-malarial agent, anti-helminthic or immunoactivator.

* * * * *